United States Patent [19]

Ackerley et al.

[11] 3,941,793
[45] Mar. 2, 1976

[54] QUINOLINE 2 CARBOXYLIC ACIDS USED IN METAL EXTRACTION PROCESSES

[75] Inventors: Norman Ackerley; Peter Albert Mack, both of Manchester, England

[73] Assignee: Imperial Chemical Industries Limited, London, England

[22] Filed: July 24, 1973

[21] Appl. No.: 382,197

[30] Foreign Application Priority Data
Aug. 4, 1972  United Kingdom............ 36560/72

[52] U.S. Cl.......... 260/287 G; 260/287 L; 260/575; 260/619 R; 260/283 CN; 423/24; 423/99; 423/139; 423/658.5; 75/101 BE
[51] Int. Cl.²....................................... C07D 215/16
[58] Field of Search..... 260/287 R, 287 GL; 423/24

[56] References Cited
UNITED STATES PATENTS

| | | | |
|---|---|---|---|
| 3,485,845 | 12/1969 | Davis et al. | 260/287 |
| 3,655,347 | 4/1972 | Mattison | 423/24 |
| 3,697,400 | 10/1972 | Pang | 260/287 |
| 3,799,930 | 3/1974 | Nakagome et al. | 260/287 |

Primary Examiner—Donald G. Daus
Assistant Examiner—David E. Wheeler
Attorney, Agent, or Firm—Cushman, Darby & Cushman

[57] ABSTRACT

Quinoline-2-carboxylic acids having in the 4-position a halogen atom or an optionally substituted hydrocarbyl group attached through an oxygen atom, optionally substituted by a hydrocarbyl group in the 3 position and optionally substituted in any of the 5, 6, 7 and 8 positions by halogen atoms, nitro or cyano groups, or optionally substituted hydrocarbyl groups each attained directly or through an oxygen atom, and containing in the substituents in the 3, 4, 5, 6, 7 and 8 positions a total of at least 3 carbon atoms form complexes with metals, especially copper. These complexes may be extracted by organic solvents from aqueous solutions of metal salts treated with the quinoline-2-carboxylic acids. The quinoline-2-carboxylic acids may be prepared from the corresponding 4-hydroxy compounds by (a) treating with a phosphorus halide, if necessary reacting the product with the alkali metal derivative of an alcohol or phenol and hydrolysing the ester group or (b) treating with a hydrocarbyl halide in presence of a base.

4 Claims, No Drawings

QUINOLINE 2 CARBOXYLIC ACIDS USED IN METAL EXTRACTION PROCESSES

This invention relates to an improved process for extracting metals from aqueous solutions containing these metals and in particular from such solutions obtained in the course of extracting metals from their ores.

One of the methods of extracting metals from these ores is to leach the ore in situ, or after mining, crushing and milling, with for example acids to give an aqueous solution of a salt of the desired metal, usually together with salts of other metals also present in the ore. The aqueous solutions may then be treated with a chelating agent which will form a complex compound with the desired metal under the conditions of treatment, which complex compound is soluble in water-immiscible organic solvents. The metal is extracted as the complex compound into a water-immiscible organic solvent which is separated from the aqueous phase. It is convenient to use a solution of chelating agent in the solvent and to carry out the treatment and extraction simultaneously. The metal may then be recovered by a variety of conventional methods from the complex. It has now been discovered that certain quinoline-2-carboxylic acids are especially valuable as chelating agents for use in this extraction method.

According to the invention there is provided a process for extracting metal values from aqueous solutions which comprises treating the aqueous solution with a quinoline-2-carboxylic acid of the formula

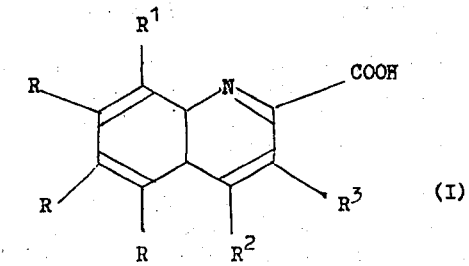

(I)

wherein each R and $R^1$, which may be the same or different, is a hydrogen or halogen atom or a cyano or nitro group or an optionally substituted alkyl, alkenyl, cycloalkyl, aralkyl, aryl, alkoxy, alkenoxy cycloalkoxy, aralkoxy, acyloxy or aryloxy group, $R^2$ is a halogen atom or an optionally substituted alkoxy, alkenoxy, cycloalkoxy, aryloxy or aralkoxy group, and $R^3$ is a hydrogen atom or an optionally substituted alkyl, alkenyl, aryl or aralkyl group, provided that the groups R, $R^1$, $R^2$ and $R^3$ contain a total of at least 3 carbon atoms, and extracting the metal in the form of a complex compound with the quinoline-2-carboxylic acid from the aqueous solution with a water-immiscible organic solvent.

As examples of halogen atoms which may be represented by R, $R^1$, or $R^2$ there are mentioned bromine and, especially, chlorine.

As examples of groups which may be represented by R there are mentioned alkyl groups such as methyl, ethyl, isopropyl, and straight chain or, preferably, branched chain higher alkyl groups such as butyl, dodecyl and nonyl, alkenyl groups such as allyl, propenyl, octenyl, dodecenyl and decenyl, cyloalkyl groups such as cyclopentyl and cyclohexyl, aralkyl groups such as benzyl, β-phenylethyl, p-dodecylbenzyl, p-nonylbenzyl, p-octylbenzyl and di-tert.-butylbenzyl, aryl groups such as phenyl, o-, m- and p-tolyl, p-nonyl phenyl, p-octylphenyl and p-tert.-butylphenyl, alkoxy groups such as methoxy, ethoxy, tert.-butoxy, tert.-pentyloxy, nonyloxy, decyloxy, dodecyloxy and octadecyloxy, alkenoxy such as allyloxy, cycloalkoxy such as cycloalkyloxy, aralkoxy such as benzyloxy, aryloxy groups such as phenoxy, tolyloxy, p-nonyl-phenoxy, and p-octylphenoxy, acyloxy groups such as acetoxy, benzoyloxy, caproyloxy, and stearoyloxy, and substituted derivatives of the above such as benzyloxy, p-dodecylbenzyloxy, p-tert.-butylphenoxy, p-nonylphenoxy and p-dodecylbenzyl. It is preferred that two of the R groups be hydrogen atoms and the third be a hydrogen or halogen atom or an alkyl group. A group R which is other than hydrogen may be in any of the positions 5, 6 or 7, but it is preferred that it be in position 6 since preparation of the 5- or 7- substituted quinolines free from each other usually presents difficulty.

As examples of groups which may be represented by $R^1$ there may be mentioned any of the groups which may be represented by R, but it is preferred that $R^1$ by a hydrogen or halogen atom or a methyl or methoxy group. Bulky groups at this position decrease very considerably the ability of the quinoline-2-carboxylic acids to form chelate complexes with metals and even small substituents such as methyl reduce the stability of the complexes to acids.

Two groups R or a group R and a group $R^1$, together may form the residue of a ring fused with the benzene ring of the quinoline-2-carboxylic acids, as for example in the 7,8-benzoquinoline-2-carboxylic acids.

As examples of groups which may be represented by $R^2$ there may be mentioned any of the alkoxy, alkenoxy, cycloalkoxy, aralkoxy or aryloxy groups or substituted derivatives thereof which may be represented by R. It is preferred that $R^2$ be a branched chain alkoxy group, for example isodecyloxy.

As examples of groups which may be represented by $R^3$ there may be mentioned any of the optionally substituted alkyl, alkenyl, aryl or aralkyl groups which may be represented by R. These quinoline-2-carboxylic acids have improved selectivity for extraction of for example copper over the corresponding compounds in which $R^3$ is a hydrogen atom since although the substitution has little effect on the stability towards acid of the copper and ferric iron complexes it reduces the stability of the cobalt, zinc, nickel and ferrous iron complexes. It is preferred that $R^3$ be an alkyl group, for example n-propyl.

It is preferred that the groups R, $R^1$, $R^2$ and $R^3$ should contain a total of from 6 to 20 aliphatic carbon atoms in order to increase solubility in the organic solvent without undue increase in molecular weight.

As examples of specific quinoline-2-carboxylic acids which may be used in the process of the invention there are mentioned 4-p-dodecylbenzyloxyquinoline-2-carboxylic acid, 4-tert.-pentyloxy-6-methylquinoline-2-carboxylic acid, 4-dodecyloxy-6-methylquinoline-2-carboxylic acid, 4-isodecyloxy-6-n-butyl-3-n-propylquinoline-2-carboxylic acid, 4-p-dodecylbenzyloxy-6-methylquinoline-2-carboxylic acid, 4-p-tert.-butylphenoxy-6-n-butylquinoline-2-carboxylic acid, 4-p-nonylphenoxy-6-n-butylquinoline-2-carboxylic acid, 4-benzyloxy-6-dodecylquinoline-2-carboxylic acid, 4- p-dodecylbenzyloxy-6-dodecylquinoline-2-carboxylic acid and 4-octadecyloxy-6-dodecylquinoline-2-carboxylic acid.

The process of the invention may be applied to the extraction of any metal which under the conditions of use, and in particular the pH of the aqueous solution, will form a stable neutral complex which will dissolve in, or will completely associate with, the organic solvent. The stability of such complexes under various pH conditions will depend primarily on the metal, that from divalent copper being in most cases stable at a pH of about 1.0 and above, and complexes from other divalent metals such as nickel, cobalt, zinc and iron being progressively less stable to acidic conditions. The formation of stable neutral complexes in the process of the invention is not restricted to metals in the divalent state or to the above metals and other metals which may form such complexes include vanadium, tin, cadmium, silver, gold and mercury.

The process of the invention is particularly suitable for the extraction of copper, nickel and cobalt from aqueous solutions leached from ores containing these metals since the quinoline-2-carboxylic acids used in the process of the invention form stable metal complexes with these metals at the low pH values normally associated with these leach liquors. By operating at pH between about 1.0 and 1.5 copper may be extracted substantially free from nickel, cobalt and iron.

It is not possible in one operation to extract for example cobalt without at the same time extracting any copper or nickel present since these metals will form stable neutral complexes in the conditions in which stable cobalt neutral complexes are obtained. It is possible by progressively increasing the pH to extract copper, nickel and cobalt selectively in that order but if, for example, it is desired to obtain cobalt from an aqueous solution containing copper and cobalt it is generally more convenient to extract both metals together and to separate the cobalt from the copper subsequently.

Since formation of the neutral complex compound usually involves the liberation of acid it may be necessary to add e.g. alkali during the process to maintain the pH within the desired range. Alternatively the quinoline-2-carboxylic acid may be used wholly or partly in the form of an alkali metal salt, although this procedure is not so suitable for continuous operation of the process.

As organic solvent there may be used any mobile organic solvent or mixture of solvents which is immiscible with water and, under the pH conditions used, inert to water, to the metallic compounds, and to the quinoline-2-carboxylic acid, for example aliphatic and aromatic hydrocarbons, halogenated hydrocarbons, esters and ethers.

In order to facilitate separation of the aqueous and solvent phases it is desirable to use a solvent having a different density from that of the aqueous layer, phase separation being in general assisted by maximising the difference in liquid densities.

When operating under conditions such that the complex is not completely soluble in the solvent but is completely associated with it, it is preferred to use solvents in which the densities of the complex and of the solvent are such that the suspended solid complex tends to gravitate away from the solvent-water interface. Examples of such solvents are dense solvents such as halogenated hydrocarbons such as perchloroethylene, trichloroethane, trichloroethylene and chloroform.

The process may conveniently be carried out by bringing together the aqueous solution and a solution of the quinoline-2-carboxylic acid or its salt in the organic solvent at a suitable temperature, conveniently ambient temperature, agitating or otherwise disturbing the mixture of liquids so that the area of the water-solvent interfacial layer is increased in order to promote complex formation and extraction, and then removing the source of agitation so that the aqueous and solvent layers settle and can be separated. The process may be carried out in a batchwise manner or continuously, in either case the solvent being if desired stripped of the metal content before re-use.

The amount of organic solvent to be used may be chosen to suit the volume of aqueous solution to be extracted, the concentration of metals, and the plant available to carry out the process. Organic aqueous volume ratios in the range 5:1 to 1:5 may in general be suitable. It is not necessary in all applications to use an amount of solvent sufficient to ensure complete solution of the complex formed, since any complex in excess of that in solution will usually remain as a suspension wholly within the organic solvent and will not interfere with the handling and separation of the solvent layer.

If desired mixtures of quinoline-2-carboxylic acids may be used, and other compounds, such as conditioners for example long chain aliphatic alcohols such as capryl alcohol, isodecanol, tridecyl alcohol or 2-ethylhexanol which assist in the formation and extraction of the complex compound, may also be present, suitably in amounts of from 0.5 to 10% by weight of the organic solvent.

The addition of surface active agents such as ethylene oxide/alkyl phenol condensates is sometimes desirable in order to assist separation of the aqueous and organic phases by reducing any tendency to emulsification.

It is preferred to use solvent solutions containing more than 2% of the quinoline-2-carboxylic acid.

The metal may be isolated from the solvent after the extraction stage by any conventional process, for example extraction into an aqueous phase using more acidic conditions under which the complex is unstable.

When complexes of more than one metal are present in the solvent separation of the metals may in some cases be achieved by extracting with separate aqueous solutions of progressively higher acidity to decompose the complexes selectively and sequentially. In an alternative procedure the complex in the solvent may be hydrogenated directly to give the metal. These treatments will regenerate the ligand and the solvent containing quinoline-2-carboxylic acid so recovered may conveniently be re-used in the process, especially when operated continuously.

The process of the invention may be applied especially to aqueous solutions resulting from treatment of mineral ores, scrap metal or other metal-containing residues with aqueous acids such as sulphuric, sulphurous, hydrochloric, hydrofluoric or nitric acids or to metal containing spent liquors from electrolytic or chemical processes. It is suitable for the recovery of metal from solutions containing at least 0.5 g. of metal per liter and particularly suitable for use with solutions containing more than 2 g. of metal per liter.

The quinoline-2-carboxylic acids used in the process of the invention are new substances and these compounds and processes for their manufacture provide further features of the invention.

The quinoline-2-carboxylic acids of the invention may be prepared from esters, preferably lower alkyl esters, or quinoline-2-carboxylic acids of formula I in which $R^2$ is a hydroxyl group by conversion of the hydroxyl group into the desired halogen atom or optionally substituted alkoxy, alkenoxy, cycloalkoxy, aryloxy or aralkyloxy group by methods known in the art for application to 4-hydroxyquinoline in general, and hydrolysis of the ester group by, for example, alkali, to afford the acid.

Quinoline-2-carboxylic acids of the formula I in which $R^2$ is a chlorine or bromine atom may be obtained from alkyl esters of quinoline-2-carboxylic acids of formula I in which $R^2$ is a hydroxyl group by heating with phosphorus oxychloride or pentachloride or phosphorus oxybromide respectively and hydrolysing the ester group.

Quinoline-2-carboxylic acids of the formula I in which $R^2$ is an optionally substituted alkoxy, alkenoxy, cycloalkyloxy, aryloxy, or aralkyloxy group may be obtained from alkyl esters of quinoline-2-carboxylic acids of formula I in which $R^2$ is a chlorine or bromine atom by heating with an alkali metal derivative of the appropriate optionally substituted alcohol or phenol and hydrolysing the ester group. The heating may conveniently be carried out in a solvent such as xylene. This method is of particular value for the preparation of quinoline-2-carboxylic acids wherein $R^3$ is an aryloxy group.

Quinoline-2-carboxylic acids of the formula I in which $R^2$ is an optionally substituted alkoxy, alkenoxy, cycloalkoxy or aralkyloxy group may be prepared from alkyl esters of quinoline-2-carboxylic acids of the formula I in which $R^2$ is a hydroxyl group by heating with the appropriate alkyl, alkenyl, cycloalkyl or aralkyl chloride or bromide in presence of a base, such as potassium carbonate, and hydrolysing the ester group. The heating may be conveniently carried out in a solvent such as acetone.

The alkyl esters of quinoline-2-carboxylic acids of formula I wherein $R^2$ is a hydroxy group used as starting materials in the above processes may be obtained for example by known methods from arylamines of the formula (II) and alkyl, for example ethyl, oxaloacyl esters of formula (III), by heating, for example in boiling toluene, to form the ethyl phenyliminosuccinate which is cyclised to the 4-hydroxyquinoline-2-carboxylic ester by heating at for example, 240°–250°C.

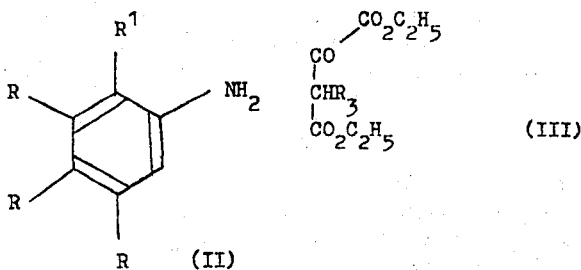

The invention is illustrated but not limited by the following examples in which all parts and percentages are by weight unless otherwise stated.

EXAMPLE 1

Approximately 180 parts of 6N.-sulphuric acid were added dropwise over 10 – 15 minutes to a well stirred mixture of 209 parts of ethyl sodio-oxalacetate, 500 parts of water and 870 parts of toluene at 0.5°C, and the resultant slightly acidic mixture (pH 3) was allowed to stir at this temperature for 45 minutes. The toluene layer was removed, the aqueous layer and precipitated sodium sulphate were washed with toluene (2 portions each comprising 65 parts), and the combined toluene layer and washings subsequently were washed acid free with water, dried over magnesium sulphate and filtered.

To the toluene solution of ethyl oxalacetate thus prepared was added 117.7 parts of p-toluidine and the mixture then was boiled under reflux during 60 minutes during which time 18 parts of water were liberated and removed with the aid of a Dean-Stark separator. After being cooled, the orange-coloured toluene solution was washed with 2N.-hydrochloric acid (3 portions each comprising 100 parts) to remove unreacted p-toluidine, then with water until acid-free, and dried over magnesium sulphate. This solution, when evaporated under reduced pressure to remove toluene, yielded 258.2 parts of ethyl (p-tolylimino) succinate, a viscous orange oil which was admixed with 110 parts of "Thermex" (a eutectic mixture of diphenyl and diphenyl oxide) and then added dropwise over 60 – 90 minutes to 1920 parts of well-stirred "Thermex" kept at 240°–250° C. After ethanol (37 parts) had been evolved and removed by distillation through a fractionation column, the dark-coloured reaction mixtue was allowed to cool and stand at room temperature for 2 – 3 days. The brown crystals (145.2 parts) which separated were collected by filtration, washed with 300 parts of light petroleum (60°–80°C) and dried in air. After purification by recrystallisation from acetone there was obtained 115.2 parts of ethyl 4-hydroxy-6-methyl quinoline-2-carboxylate, small pale-buff coloured needles m.pt. 214°–216°C; by concentration of the acetone mother liquors 13.9 parts of less pure product, m.pt. 207°–208°C, were obtained.

A well-stirred mixture of 34.65 parts of ethyl 4-hydroxy-6-methyl quinoline-2-carboxylate, 21 parts of anhydrous potassium carbonate, 46.5 parts of 4-dodecylbenzyl chloride (prepared by the method described in U.S. Pat. No. 2,630,459 from a highly-branched dodecyl-substituted benzene, chlorosulphonic acid, methanol and paraformaldehyde), and 615 parts of anhydrous acetone was boiled under reflux for 68 hours. The cooled, brown-coloured reaction mixture was filtered to remove inorganic salts and unreacted ethyl 4-hydroxy-6-methyl quinoline-2-carboxylate (3.7 parts) and acetone was removed by evaporation under reduced pressure. A solution of the residual brown oil in ether (285 parts) was washed successively with N.-sodium hydroxide (2 portions each comprising of 50 parts) and water (2 portions each comprising 50 parts), then dried over magnesium sulphate, and evaporated to remove solvent. There then remained 69.2 parts of ethyl 6-methyl-4 (4'-dodecylbenzyloxy) quinoline-2-carboxylate, a viscous brown oil, which was dissolved in 120 parts of ethanol and then boiled under reflux for 2.5 hours with a solution containing 6 parts of sodium hydroxide in 25 parts of water. After the reaction mixture had been cooled to 0°C, the sodium salt of 6-methyl-4-(4'-dodecylbenzyloxy) quinoline-2-carboxylic acid, which separated as a colourless granular solid (53.4 parts), was collected by filtration, washed with 25 parts of ethanol and dried.

34.2 parts of the sodium salt of 6-methyl-4-(4'-dodecylbenzyloxy) quinoline-2-carboxylic acid were suspended in 750 parts of chloroform containing 50 parts of glacial acetic acid. After the mixture had been shaken vigorously for 10 minutes 200 parts of water were added, agitation was continued for a further 5 minutes, and the lower chloroform layer was separated off. This organic layer was shaken repeatedly with 10% W/V aqueous acetic acid (5 portions each comprising 50 parts), then with water (100 part portions) until acid-free and dried over magnesium sulphate. Chloroform was removed from the filtered solution by evaporation under reduced pressure, and the residual viscous residue was heated at 85°C/20 mm pressure during 4 hours to ensure removal of all solvent. On cooling the viscous oil solidified to yield 30.8 parts of 6-methyl-4-(4'-dodecylbenzyloxy) quinoline-2-carboxylic acid as a pale buff-coloured solid mass, m.pt. 95°–96°C (softening at ca. 70°C) (Found: C 78.7, H 8.1, N 2.6%. $C_{30}H_{39}NO_3$ requires C 78.1, H 8.5, N 3.0%).

EXAMPLE 2

By the procedure of Example 1 using p-butylaniline instead of p-toluidine there were obtained ethyl 4-hydroxy-6-n-butylquinoline-2-carboxylate, m.pt. 165°C, and 6-n-butyl-4-(4'dodecylbenzyloxy) quinoline-2-carboxylic acid, a highly viscous pale brown gum.

EXAMPLE 3

126 parts of ethyl 4-hydroxy-6-n-butylquinoline-2-carboxylate, prepared as described in Example 2, and 213 parts of phosphorus oxychloride were stirred together. After the exothermic reaction had subsided the dark-coloured mixture was stored for 1 hour at room temperature then cooled to 0°C, diluted with 75 parts of ethanol to improve its mobility and subsequently added dropwise to 500 parts of ice and 1500 parts of water. The aqueous mixture was neutralised to pH 7 – 8 by addition of sodium carbonate when 133.2 parts of a light brown coloured crystalline solid separated out and were collected by filtration and dried. This material was purified by recrystillisation from about 380 parts of acetone (with carbon treatment) and yielded 100.8 gm. of ethyl 4-chloro-6-n-butylquinoline-2-carboxylate which was isolated as pale grey needles, m.pt. 58°–58.5°C. An additional 27.5 parts of less pure product, m.pt. 54.5°–56°C, was obtained by dilution of the acetone mother-liquor with water.

4-chloro-6-n-butylquinoline-2-carboxylic acid, prepared in the conventional manner from the ethyl ester (43.7 parts) by hydrolysis with boiling 20% sodium hydroxide and then acidification, separated from aqueous ethanol in colourless needles (28.7 parts), m.pt. 117.5°–119°C. (Found: C 63.2, H 5.5, N 4.5, Cl 13.5% $C_{14}H_{14}NO_2Cl$ requires C 63.8, H 5.35, N 5.3, Cl 13.45%).

A well-stirred mixture of 55 parts of 4-nonyl phenol (mixed branched-chain isomers, obtained by alkylation of phenol with propylene trimers), 870 parts of xylene, and a solution of 20 parts of sodium hydroxide in 25 parts of water was boiled under reflux for 4½ hours and dehydrated with the aid of a Dean-Stark separator. 72.9 parts of ethyl 4-chloro-6-n-butyl-quinoline-2-carboxylate than were introduced and the anhydrous mixture was boiled under reflux for 40 hours. Xylene was removed by distillation in steam and the aqueous mother liquors were decanted (whilst still hot) from the residual light brown-coloured rubbery mass which then was washed with 1200 parts of water and suspended in 1500 parts of chloroform. 100 parts of glacial acetic acid were introduced into this suspension of sodium salts which was stirred for 60 minutes and then treated with 200 parts of water. The aqueous layer was removed and the resultant chloroform solution was washed with successive portions of 10% aqueous acetic acid (4 portions each comprising 200 parts) and then water (200 part portions) until acid-free. After being dried over magnesium sulphate the chloroform solution was evaporated under reduced pressure to yield 120.1 parts of a clear, red-coloured viscous oil which was dissolved in 500 parts of ethanol and then boiled under reflux for 30 – 60 minutes with a solution containing 12.5 parts of sodium hydroxide in 25 parts of water and 20 parts of ethanol. After the reaction mixture had been cooled and allowed to stir overnight at room temperature, 95.1 parts of the sodium salt of 6-n-butyl-4-(4'-nonylphenoxy)quinoline-2-carboxylic acid, which has seperated as a light buff-coloured granular solid, were collected by filtration, washed with 85% ethanol (100 parts) and dried in vacuo.

95.1 parts of the sodium salt of 6-n-butyl-4-(4'-nonylphenoxy)quinoline-2-carboxylic acid were suspended in 750 parts of chloroform containing 35 parts of glacial acetic acid. After the mixture had been shaken vigorously for 10 minutes, 200 parts of water were added, agitation was continued for a further 5 minutes and the lower chloroform layer was separated off. This organic layer was shaken repeatedly with 10% W/V aqueous acetic acid (5 portions each comprising 50 parts), then with water (100 part portions) until acid-free and dried over magnesium sulphate. Chloroform was removed from the filtered solution by evaporation under reduced pressure and there remained 91.6 parts of 6-n-butyl-4-(4'-nonylphenoxy) quinoline-2-carboxylic acid, a clear red-coloured viscous oil, the structure of which was demonstrated by its spectral breakdown pattern.

EXAMPLE 4

By the procedure of Example 3 using 2-tert.-butyl-4-methylphenol instead of 4-nonylphenol there was obtained 6-n-butyl-4-(2'-tert.-butyl-4'-methylphenoxy) quinoline-2-carboxylic acid, a red-coloured viscous gum.

EXAMPLE 5

By the procedure of Example 3 using 2-tert.-butyl-5-methylphenol instead of 4-nonylphenol there was obtained 6-n-butyl-4-(2'-tert.-butyl-4'-methylphenoxy) quinoline-2-carboxylic acid, a red-brown viscous gum.

EXAMPLE 6

By the procedure of Example 3 using 2,4-di-tert.-pentylphenol instead of 4-nonylphenol there was obtained 6-n-butyl-4-(2',4'-ditert-pentylphenoxy) quinoline-2-carboxylic acid, a brown coloured viscous gum.

EXAMPLE 7

The method of Example 6 was repeated using 17.0 parts of 4-phenyl phenol in place of the 2,4-ditert-pentylphenol. There were obtained 35.4 parts of 6-n-butyl-4-(4'-phenylphenoxy) quinoline-2-carboxylic acid, as a viscous dark-coloured oil.

EXAMPLE 8

The method of Example 6 was repeated using 17.5 parts of 4-cyclohexylphenol in place of the 2,4-ditert-pentylphenol. There were obtained 11.7 parts of 6-n-butyl-4-(4'-cyclohexylphenoxy) quinoline-2-carboxylic acid as an extremely viscous, dark-coloured oil.

EXAMPLE 9

44.2 parts of 2,6-ditert.-butyl-4-methylphenol and a solution comprising 22.4 parts of potassium hydroxide, 16 parts of water, and 50 parts of methanol were boiled together under reflux in an atmosphere of nitrogen until all the phenol had dissolved. 400 parts of xylene and 58.3 parts of ethyl 4-chloro-6-n-butyl quinoline-2-carboxylate (as prepared in Example 3) then were introduced and the heating was continued for 20 hours whilst the inert atmosphere was maintained. After 400 parts of water had been added, xylene and methanol were removed in steam and the mixture was allowed to cool. The aqueous phase was decanted from the residual sticky solid which was then washed with water and suspended in 300 parts of chloroform. The chloroform suspension was treated with 30 parts of acetic acid, the mixture was shaken for 10 minutes and then 100 parts of water were added. After the aqueous layer had been removed, the chloroform solution was washed repeatedly with 10% W/V aqueous acetic acid (3 portions each comprising 200 parts) then with water (200 part portions) until acid-free, and dried over magnesium sulphate. Chloroform was removed from the filtered solution by evaporation under reduced pressure and there remained 69.7 parts of a viscous, red-coloured gummy product which largely crystallised during storage. When recrystallised from light petroleum (60°-80°C) this material yielded 42.4 parts of 6-n-butyl-4-(2',6'-ditert.-butyl-4'-methylphenoxy) quinoline-2-carboxylic acid, pale pink needles m.p. 95°-98°C.

EXAMPLE 10

By the procedure of Example 1 using p-chloroaniline instead of p-toluidine there was obtained ethyl 6-chloro-4-hydroxy quinoline-2-carboxylate, which was converted by the procedures of Example 3 into ethyl 4,6-dichloroquinoline-carboxylate, m.pt. 108°-110°C, and then, using 4-nonylphenol, into 4,6-di-(4'-nonylphenoxy)-quinoline-2-carboxylic acid, a viscous light-reddish-brown coloured oil.

EXAMPLE 11

By the procedure of Example 1 using p-anisidine instead of p-toluidine there were obtained ethyl 4-hydroxy-6-methoxyquinoline-2-carboxylate, m.pt. 209°-212°C, and ethyl 6-methoxy-4-(4'-dodecylbenzoyloxy)-quinoline-2-carboxylate, a viscous brown oil, and 6-methoxy-4-(4'-dodecylbenzyloxy)-quinoline-2-carboxylic acid, a light-brown viscous oil.

EXAMPLE 12

Ethyl 4-hydroxy-6-methoxyquinoline-2-carboxylate, prepared as described in Example 11, is converted by the procedures of Example 3 into ethyl 4-chloro-6-methoxyquinoline-2-carboxylate, m.p. 91.5°-92.5°C, 4-chloro-6-methoxyquinoline-2-carboxylic acid, m.p. 189.5°C with decomposition, and 6-methoxy-4-(4'-nonylphenoxy) quinoline-2-carboxylic acid, a pale yellow semi-solid product.

EXAMPLE 13

By the procedure of Example 1 using o-toluidine instead of p-toluidine there were obtained ethyl 4-hydroxy-8-methylquinoline-2-carboxylate, m.p. 138°-139°C, and 8-methyl-4-(4'-dodecylbenzyloxy)-quinoline-2-carboxylic acid, a viscous brown oil.

EXAMPLE 14

Ethyl 4-hydroxy-8-methylquinoline-2-carboxylate, prepared as described in Example 13, was converted by the procedures of Example 3 into ethyl 4-chloro-8-methylquinoline-2-carboxylate, m.p. 66°-68°C, and a mixture of 4-chloro-8-methylquinoline-2-carboxylic acid, m.p. 175°C with decomposition, and 8-methyl-4-(4'-nonylphenoxy)quinoline-2-carboxylic acid, m.p. 121°-123°C, separated by treatment with hot light petroleum in which the former is comparatively insoluble. Reactions of 8-methyl-4-(4'-nonylphenoxy) quinoline-2-carboxylic acid with copper or cobalt acetate in boiling ethanol or methanol afforded the copper complex, green, m.p. 192°-193°C with decomposition, or the cobalt complex, purple, m.p. 264°-266°C with decomposition, the compositions being in each case confirmed by microanalysis.

EXAMPLE 15

By the procedures of Example 1 using 4-methoxy-o-toluidine instead of p-toluidine there were obtained ethyl 4-hydroxy-6-methoxy-8-methylquinoline-2-carboxylate, m.p. 149.5°-150.5°C and 6-methoxy-8-methyl-4-(4'-dodecylbenzyloxy)quinoline-2-carboxylic acid, a cream coloured semi-solid product.

EXAMPLE 16

By the procedures of Example 1 using 4-chloro-o-toluidine instead of p-toluidine there were obtained ethyl 4-hydroxy-6-chloro-8-methylquinoline-2-carboxylate, m.p. 123°-124.5°C, and 6-chloro-8-methyl-4-(4'-dodecylbenzyloxy)quinoline-2-carboxylic acid, a yellow semi-solid product.

EXAMPLE 17

By the procedure of Example 1 using o-chloroaniline instead of p-toluidine there were obtained ethyl 8-chloro-4-hydroxyquinoline-2-carboxylate, m.p. 143°-145°C, and, using benzyl chloride instead of dodecylbenzyl chloride, ethyl 8-chloro-4-benzyloxyquinoline-2-carboxylate, m.p. 143°-144°C, and 8-chloro-4-benzyloxyquinoline-2-carboxylic acid, m.p. 187°C with decomposition.

EXAMPLE 18

By the procedure of Example 1 using ethyl ethoxalyl propionate instead of ethyl oxalacetate and p-butylaniline instead of p-toluidine there were obtained, using a few drops of hydrochloric acid as catalyst in the initial condensation stage, ethyl 3-methyl-4-hydroxy-6-n- butylquinoline-2-carboxylate, m.p. 156°–157°C and 3-methyl-6-n-butyl-4-(4'-dodecylbenzyloxy)quinoline-2-carboxylic acid, a pale orange viscous oil.

EXAMPLE 19

By the procedure of Example 18 using aniline instead of p-butylaniline there were obtained ethyl 3-methyl-4-hydroxyquinoline-2-carboxylate, m.p. 175°–177°C, and 3-methyl-4-(4'-dodecylbenzyloxy) quinoline-2-carboxylic acid, a pale yellow oil.

EXAMPLE 20

By the procedure of Example 18 using o-toluidine instead of p-butylaniline there were obtained ethyl 3,8-dimethyl-4-hydroxyquinoline-2-carboxylate, m.p. 133°–134°C and 3,8-dimethyl-4-(4'-dodecylbenzyloxy)quinoline-2-carboxylic acid, a viscous pale yellow oil.

EXAMPLE 21

A well-stirred mixture of 65.1 parts of ethyl-4-hydroxy-quinoline-2-carboxylate, 42 parts of anhydrous potassium carbonate, 38.4 parts of allyl bromide and 800 parts of acetone was boiled under reflux for 24 hours. The cooled reaction mixture was filtered to remove inorganic salts and acetone was removed by evaporation under reduced pressure. A solution of the residual brown oil in ether (360 parts) was washed successively with N-sodium hydroxide solution (3 portions each comprising 50 parts) and water (4 portions each of 100 parts), then dried over magnesium sulphate and evaporated to remove solvent. The resultant viscous oil crystallised on cooling and the crystals were recrystallised from light petroleum (60°–80°C) to yield 57.1 parts of ethyl 4-allyloxyquinoline-2-carboxylate as pale yellow needles, m.pt. 71°–72°C.

A well-stirred mixture of 61.4 parts of ethyl 4-allyloxy quinoline-2-carboxylate and 320 parts of "Shellsol T" (an aliphatic kerosine) was heated at 180°–190°C for 2 hours under an atmosphere of nitrogen. After cooling while stirring the reaction mixture was filtered and the solid product washed with 50 parts of light petroleum and crystallised from toluene to yield ethyl 3-allyl-4-hydroxyquinoline-2-carboxylate (49.2 parts) as almost colourless needles, m.pt. 146.5°–147°C. A small sample after further purification from ethanol formed large rhombic prisms, m.pt. 148.5°–150°C. (Found: C 69.7; H 4.9; N 5.0%. $C_{15}H_{15}NO_3$ requires C 70.0; H 5.9; N 5.4%).

A solution of 49.0 parts of ethyl 3-allyl-4-hydroxy-quinoline-2-carboxylate in 600 parts of boiling ethanol was stirred for 5 minutes in 3 parts of 3% palladium-on-carbon catalyst, then filtered and the filtrate together with 5 parts of fresh catalyst was charged to a stainless steel autoclave and hydrogen added at room temperature to a pressure of 50 atmospheres. After stirring at 16 hours 1.38 moles of hydrogen had been absorbed. The reaction mixture was dissolved in hot ethanol, filtered to remove catalyst, and evaporated to give 39.3 parts of ethyl 3-n-propyl-4-hydroxyquinoline-2-carboxylate, pale yellow needles, m.pt. 155°–157°C which were collected and dried; a further 4.8 parts of less pure product m.pt. 140°–146°C were recovered from the ethanolic mother liquors after concentration in vacuo. After repeated recrystallisation from ethanol very pale yellow prismatic needles, m.pt. 158°–159.5°C were obtained. (Found: C 69.3; H 6.3; N 5.2%. $C_{15}H_{17}NO_3$ requires C 69.5; H 6.6; N 5.4%).

3-n-Propyl-4-hydroxyquinoline-2-carboxylic acid prepared in the conventional manner from the ethyl ester by hydrolysis with boiling 12% w/v potassium hydroxide solution and then acidification, separated from 50% ethanol in fine colourless needles, m.pt. 194°–195°C (decomp.) (Found: C 67.1; H 5.7; N 6.2%. $C_{13}H_{13}NO_3$ requires C 67.5; H 5.7; N 6.1%).

A well-stirred mixture of 5 parts of ethyl 3-n-propyl-4-hydroxyquinoline-2-carboxylate, 3 parts of anhydrous potassium carbonate and 3.3 parts of benzyl bromide in anhydrous acetone was boiled under reflux for 16 hours, filtered to remove inorganic salts, and evaporated to remove solvent. A solution of the residual oil in 75 parts of ether, after being washed with N.sodium hydroxide (2 portions each comprising 25 parts) and then water (4 portions each of 40 parts) was dried over magnesium sulphate and evaporated to yield 6.4 parts of crude ethyl 3-n-propyl-4-benzyloxyquinoline-2-carboxylate as a very pale yellow oil.

This material dissolved in 32 parts of boiling ethanol was hydrolysed during 2 hours with 5 parts of 16% aqueous sodium hydroxide, then evaporated to remove most of the ethanol, diluted with 150 parts of water and acidified with glacial acetic acid. The initially-formed oily precipitate slowly crystallised on keeping at 0°C to yield 5.1 parts of crude product, m.pt. 127°–129°C, which upon recrystallisation from ethanol gave 3.9 parts of 3-n-propyl-4-benzyloxyquinoline-2-carboxylic acid, rosettes of colourless needles m.pt. 139°–140°C (decomp.) (Found: C 74.4; H 6.0; N 3.6%. $C_{20}H_{19}NO_3$ requires C 74.7; H 6.0; N 4.4%).

EXAMPLE 22

Ethyl 3-n-propyl-4-hydroxyquinoline-2-carboxylate, prepared as described in Example 21, was converted by the procedures of Example 3, using reflux temperatures in the first stage to complete the reaction, into ethyl 3-n-propyl-4-chloroquinoline-2-carboxylate, a viscous oil, and 3-n-propyl-4-(4'-nonylphenoxy)-quinoline-2-carboxylic acid, a red semi-solid.

EXAMPLE 23

By the procedure of Example 1 using ethyl ethoxalylvalerate instead of ethyl oxalacetate and aniline instead of p-toluidine there were obtained, using a few drops of hydrochloric acid as catalyst in the initial condensation stage, ethyl 3-n-propyl-4-hydroxyquinoline-2-carboxylate, identical with the product prepared by the procedure of Example 21, and 3-n-propyl-4-(4'-dodecylbenzyloxy)-quinoline-2-carboxylic acid, a viscous pale-orange oil.

EXAMPLE 24

Ethyl 4-hydroxy-6-n-butylquinoline-2-carboxylate was converted by the procedures of Example 21 into ethyl-4-allyloxy-6-n-butylquinoline-2-carboxylate, a viscous brown oil, ethyl-3-allyl-4-hydroxy-6-n-butylquinoline-2-carboxylate, m.p. 156°–157.5°C, ethyl 3-n-propyl-4-hydroxy-6-n-butylquinoline-2-carboxylate, m.p. 136°–137°C, and 3-n-propyl-6-n-butyl-4-(4'-dodecylbenzyloxy)quinoline-2-carboxylic acid, a viscous pale-yellow oil.

EXAMPLE 25

Ethyl 3-n-propyl-6-n-butyl-4-hydroxyquinoline-2-carboxylate was converted by the procedure of Example 22 into ethyl 3-n-propyl-6-n-butyl-4chloro-quinoline-2-carboxylate, m.p. 43.5°–44°C, and 3-n-propyl-6- n-butyl-4-(4'-nonylphenoxy)quinoline-2-carboxylic acid, a viscous brown oil.

EXAMPLE 26

Ethyl 6-n-butyl-4-hydroxyquinoline-2-carboxylate was converted by the procedures of Example 21 using isodecyl bromide instead of allyl bromide into ethyl 4-isodecyloxy-6-n-butylquinoline-2-carboxylate, a viscous brown oil, and 4-isodecyloxy-6-n-butyl quinoline-2-carboxylic acid, cream-coloured semi-solid.

EXAMPLE 27

Ethyl 3-n-propyl-6-n-butyl-4-hydroxyquinoline-2-carboxylate was converted by the procedure of Example 26 into ethyl 3-n-propyl-6-n-butyl-4-isodecyloxyquinoline-2-carboxylate and 3-n-propyl-6-n-butyl-4-isodecyloxyquinoline-2-carboxylic acid, pale brown viscous oil.

EXAMPLE 28

By the procedure of Example 23 using ethyl ethoxalylphenylacetate instead of ethyl ethoxalylvalerate and p-n-butylaniline instead of aniline there were obtained ethyl 3-phenyl-4-hydroxy-6-n-butylquinoline-2-carboxylate, m.p. 164°–165°C, and 3-phenyl-6-n-butyl-4-(4'-dodecylbenzyloxy)quinoline-2-carboxylic acid, a viscous brown oil.

EXAMPLE 29

By the procedure of Example 28 using ethyl ethoxalylbenzylacetate instead of ethyl ethoxalylphenylacetate there were obtained ethyl 3-benzyl-6-n-butyl-4-hydroxyquinoline-2-carboxylate, m.p. 163.5°–164.5°C, and 3-benzyl-6-n-butyl-4-(4'-dodecylbenzyloxy)quinoline-2-carboxylic acid, a viscous yellow-orange oil.

EXAMPLE 30

By the procedure of Example 1 using p-isodecylaniline instead of p-toluidine there were obtained ethyl 6-isodecyl-4-hydroxyquinoline-2-carboxylate, a very viscous brown oil, and 6-isodecyl-4-(4'-dodecyloxybenzyl)quinoline-2-carboxylic acid, a viscous brown gum.

EXAMPLE 31

Ethyl 6-chloro-4-hydroxyquinoline-2-carboxylate was converted by the procedure described in Example 1 to 6-chloro-4-(4'-dodecylbenzyloxy)quinoline-2-carboxylic acid, viscous light-brown oil.

EXAMPLE 32

A vigorously-agitated mixture comprising 25 ml of a chloroform solution nominally containing $0.5 \times 10^{-3}$ moles of quinoline-2-carboxylic acid (ligand) and 25 ml of an aqueous acidic solution of the appropriate metal ion ($0.25 \times 10^{-3}$ moles for a divalent metal; $0.1667 \times 10^{-3}$ moles for a trivalent metal) and also containing $0.25 \times 10^{-3}$ moles of perchloric acid, was titrated potentiometrically against N-sodium hydroxide solution. A similar experiment was also conducted using 25 ml of the pure chloroform solvent. From the difference between the two resultant pH-titration curves, the percentage of complex formation between the ligand and a given metal ion was determined for a range of pH values (2:1 ligand/metal stoichiometry was assumed for divalent metals; 3:1 for trivalent metals) and a third curve was constructed relating percentage complex formation and pH. From this latter curve the $pH_{50}$ value was determined, this value being defined as the pH at which 50% of the total observable (not theoretical) complex formation occurred.

Sulphate ions were present additionally in all the metal solutions since these were prepared from the appropriate metal sulphates. However in the case of iron (II), iron (III), and aluminium solutions, ammonium ions also were present since it was expedient to use the ammonium metal double salts.

The results are given in Table I.

TABLE I

| Quinoline-2-carboxylic acid Example number | METAL | | | | | |
| --- | --- | --- | --- | --- | --- | --- |
| | Cu | Fe(III) | Zn | Co | Ni | Fe(II) |
| 1 | 1.0 | 1.6 | 2.0 | 2.0 | 2.4 | 2.4 |
| 3 | <1.0 | 1.0 | 1.8 | 1.8 | 2.0 | 2.3 |
| 4 | 1.0 | — | 1.75 | 1.85 | — | — |
| 5 | 1.0 | 1.2 | Indef. | 1.4 | 1.5 | 1.6 |
| 6 | 1.4 | — | — | 1.95 | 2.15 | — |
| 7 | 1.3 | Indef. | 1.45 | 1.65 | — | — |
| 8 | 1.1 | Indef. | 1.8 | 1.8 | — | — |
| 9 | Indef. | Indef. | 1.25 | 1.3 | — | — |
| 10 | <1.0 | 1.1 | 1.6 | 1.6 | 2.2 | 2.1 |
| 11 | 1.45 | — | 2.05 | 2.0 | — | — |
| 12 | <1.0 | 1.1 | 1.85 | 2.0 | Indef. | Indef. |
| 13 | 2.6 | None | 4.6 | None below pH 6 | — | — |
| 14 | 2.6 | None | 4.6 | 5.9 | 5.95 | None below pH 6 |
| 15 | 2.7 | None | 4.1 | None below pH 6 | — | — |
| 16 | 2.8 | None | 4.2 | None below pH 6 | — | — |
| 17 | 1.6 | None | 3.0 | 4.5 | 4.2 | Indef. |
| 18 | <1.0 | 1.25 | 2.6 | 2.8 | 2.65 | 3.2 |
| 19 | <1.0 | 1.1 | 2.1 | 2.9 | 2.5 | 3.2 |
| 20 | 3.2 | None | 5.3 | 6.0 | None below pH 6 | None |
| 22 | 1.1 | Indef. | 2.85 | 2.85 | — | — |
| 24 | Indef. | 1.55 | 3.85 | 4.2 | — | — |
| 25 | <1.0 | 1.3 | 2.5 | 2.8 | 2.6 | 3.0 |
| 26 | <1.0 | Indef. | 2.0 | 2.2 | 2.0 | 2.7 |
| 27 | <1.0 | 1.5 | 2.7 | 2.9 | 2.9 | 3.3 |
| 28 | <1.0 | 1.6 | 2.5 | 2.9 | 2.8 | 3.2 |
| 29 | 1.1 | 1.1 | 3.1 | 3.35 | — | — |
| 30 | 1.2 | 1.8 | 2.1 | 2.1 | 2.5 | 2.65 |
| 31 | <1.0 | — | — | 1.9 | — | — |

None indicates no complex formation.
Indef. values were due to severe emulsification difficulties.
— indicates no measurement was made.

EXAMPLE 33

A 100 ml portion of a 3.13% weight/volume solution of 6-methyl-4-(4'-dodecylbenzyloxy)quinoline-2-carboxylic acid in perchloroethylene (concentration equivalent to a cobalt concentration of 2 gm/liter) was intimately contacted at 50°C for 10 minute periods with 3 successive 100 ml portions of a solution of heavy metal sulphates in dilute sulphuric acid, initially at pH 2.0, in which the original concentrations of cobalt and iron (II) ions were 2.0 g/liter and those of zinc and copper were 0.2 g/liter and 0.05 g/liter respectively and allowed to separate. The metal ion concentrations in the three aqueous solutions after extraction (raffinates) then were determined by atomic absorption spectrophotometry.

The metal-loaded organic layer subsequently was back-washed successively with 25 ml portions of dilute sulphuric acid in which the sulphuric acid concentrations were 10 g/liter and 150 g/liter respectively, and the metal concentrations in the two resultant acid extracts again were measured by the atomic absorption method. The results are indicated in the following Table.

EXAMPLE 34

A 25 ml portion of a solution of cobalt sulphate and dilute sulphuric acid initially at pH 2.0 and with a cobalt concentration of 2 g/liter, was intimately contacted at room temperature for 5 minute periods with three successive 25 ml portions of a 3.42% (weight/volume) solution of 6-n-butyl-4-(4'-dodecylbenzyloxy)quinoline-2-carboxylic acid in "Shellsol T" (concentration equivalent to a cobalt concentration of 2 g/liter) and allowed to separate. The metal content and pH of the aqueous phase was determined after each contacting and separation and the results were as follows:

| Aqueous solution | Co content (g/liter) | pH |
|---|---|---|
| Initially | 2.0 | 2.0 |
| After 1st Ligand treatment | 1.24 | 1.65 |
| After 2nd Ligand treatment | 0.95 | 1.54 |
| After 3rd Ligand treatment | 0.76 | 1.46 |

EXAMPLE 35

The procedure of Example 33 was repeated using a 3.42% (weight/volume) solution of 6-n-butyl-4-(4'-dodecylphenyloxy) quinoline-2-carboxylic acid in the "Shellsol T" at room temperature.

The results are indicated in the following table.

|  | Metal Ion Concentration In Aqueous Liquors (g/liter) | | | |
|---|---|---|---|---|
|  | Co | Fe(II) | Zn | Cu |
| Metal-Loading of Ligand Solution | | | | |
| Original solution of metal sulphates at pH 2.0 | 2.0 | 2.0 | 0.20 | 0.05 |
| Aqueous raffinate I | 1.39 | 1.75 | 0.15 | 0.001 |
| Aqueous raffinate II | 1.76 | 1.88 | 0.20 | 0.0003 |
| Aqueous raffinate III | 1.87 | 1.86 | 0.20 | 0.002 |
| Total metals extracted into organic phase (by difference) | 0.98 | 0.51 | 0.05 | 0.15 |
| Acid-Stripping of Metal-Loaded Ligand Solution | | | | |
| Acid Strip Liquors (10 g/l H$_2$SO$_4$) | 0.89 | 0.10 | 0.038 | 0 |
| Acid Strip Liquors (150 g/l H$_2$SO$_4$) | 0.07 | 0.09 | 0.005 | 0.139 |
| Total metals extracted from loaded organic phase by 2 acid strips | 0.96 | 0.19 | 0.04 | 0.14 |

They clearly demonstrate selective back-washing of cobalt and zinc over copper and to a lesser extent iron (II) from a metal-loaded ligand solution by weak sulphuric acid of strength 10 g/liter rather than by stronger acid (150 g/liter).

|  | Metal Ion Concentration In Aqueous Liquors (g/liter) | | | | pH |
|---|---|---|---|---|---|
|  | Co | Fe(III) | Zn | Cu | |
| Metal-Loading of Ligand Solution | | | | | |
| Original solution of metal sulphates at pH 2.0 | 2.0 | 2.0 | 0.20 | 0.05 | 2.0 |
| Aqueous raffinate I | 1.59 | 1.77 | 0.153 | 0 | 1.68 |
| Aqueous raffinate II | 1.95 | 1.72 | 0.204 | 0 | 1.94 |
| Aqueous raffinate III | 2.07 | 1.71 | 0.200 | 0 | 2.0 |
| Total metals extracted into | 0.39 | 0.80 | 0.043 | 0.15 | |

-continued

| | Metal Ion Concentration In Aqueous Liquors (g/liter) | | | | pH |
|---|---|---|---|---|---|
| | Co | Fe(III) | Zn | Cu | |
| organic phase (by difference) Acid-Stripping of Metal-Loaded Ligand Solution | | | | | |
| Acid strip liquors (10 g/l H$_2$SO$_4$) | 0.327 | 0.218 | 0.039 | 0.001 | |
| Acid strip liquors (150 g/l H$_2$SO$_4$) | 0.006 | 0.018 | 0.001 | 0.08 | |
| Total metals extracted from loaded organic phase by 2 acid strips | 0.33 | 0.24 | 0.040 | 0.081 | |

The results demonstrate selective back-washing of cobalt and zinc over copper and to a lesser extent iron (III) from a metal-loaded ligand solution by weak sulphuric acid of strength 10 g/liter rather than by stronger acid (150 g/liter).

EXAMPLE 36

The procedure of Example 34 was repeated using 50 ml of a solution of cobalt sulphate (2 g/liter) at pH 2.0 and a 4.55% (weight/volume)solution of 6-n-butyl-4(4'-nonylphenoxy)quinoline-2-carboxylic acid in perchloroethylene (equivalent to 3.0 g of cobalt per liter). The results were as follows.

| Aqueous solution | Co Content (g/liter) | pH |
|---|---|---|
| Initially | 2.0 | 2.0 |
| After 1st Ligand treatment | 0.895 | 1.45 |
| After 2nd Ligand treatment | 0.452 | 1.32 |
| After 3rd Ligand treatment | 0.242 | 1.25 |

EXAMPLE 37

A 50 ml portion of a 3.03% (weight/volume) solution of 6-n-butyl-4-(4'-nonylphenoxy)quinoline-2-carboxylic acid in "Shellsol T" (equivalent to a cobalt concentration of 2 g/liter) was intimately contacted at room temperature for 5 minute periods with 3 successive 50 ml portions of a solution of heavy metal sulphates in dilute sulphuric acid initially at pH 2.0, which the original concentration of cobalt was 2.0 g/liter, and those of iron (II), iron (III), zinc annd copper were 1.56, 0.44, 0.2 and 0.05 g/liter respectively. After separation the metal concentrations in the three aqueous raffinates then were determined by atomic absorption spectrophotometry.

The metal-loaded organic solution was divided into two portions of equal volume, one of which was well-washed for 5 minutes with a 25 ml portion of sulphuric acid of strength 30 g/liter whilst the second was treated similarly with sulphuric acid of strength 150 g/liter, the metal concentrations in both acid washings then being determined by the atomic absorption method. The results are indicated in the following table.

| | Metal Ion Concentration in Aqueous Liquors (g/liter) | | | |
|---|---|---|---|---|
| | Co | Fe(II) + Fe(III) | Zn | Cu |
| Metal-Loading of Ligand Solution | | | | |
| Original solution of metal sulfates at pH 2.0 | 2.0 | 2.0 | 0.20 | 0.05 |
| Aqueous raffinate I | 1.616 | 1.648 | 0.145 | 0 |
| Aqueous raffinate II | 2.0 | 1.760 | 0.216 | 0.014 ppm |
| Aqueous raffinate III | 2.0 | 1.804 | 0.218 | 11.5 ppm |
| Total metals extracted into organic phase (by difference) | 0.384 | 0.788 | 0.021 | 0.15 |
| Acid-Strip of Metal-Loaded Ligand solution | | | | |
| Acid strip liquors (30 g/liter H$_2$SO$_4$) | 0.347 | 0.775 | 0.021 | 1.5 ppm |
| Acid strip liquors (150 g/liter H$_2$SO$_4$) | 0.35 | 0.78 | 0.021 | 0.022 |

EXAMPLE 38

A 25 ml portion of a 16.88% (weight/volume) solution of 6-n-butyl-4-(4'-nonylphenoxy)quinoline-2-carboxylic acid in "Shellsol T" (equivalent to a copper concentration of 12.0 g/liter) was intimately contacted for 5 minute periods and then allowed to separate with 3 successive 25 ml portions of a solution of heavy metal sulphates in dilute sulphuric acid initially at pH 2.0, in which the original concentration of copper was 11.25 g/liter, those of iron (III) and cobalt were 0.25 g/liter and that of zinc was 0.05 g/liter. The metal-loaded organic solution then was washed with a 25 ml portion of sulphuric acid of strength 150 g/liter. The metal concentrations in the three aqueous raffinates and in the sulphuric acid strip liquors were determined by atomic absorption spectrophotometry. The results are presented in the following table.

|  | Metal Ions Concentration in Aqueous Liquors (g/liter) | | | |
| --- | --- | --- | --- | --- |
|  | Cu | Fe(III) | Co | Zn |
| Metal-Loading of Ligand Solution |  |  |  |  |
| Original solution of metal sulphates at pH 2.0 | 11.250 | 0.250 | 0.250 | 0.050 |
| Aqueous raffinate I | 3.362 | 0.250 | 0.247 | 0.050 |
| Aqueous raffinate II | 11.083 | 0.240 | 0.251 | 0.049 |
| Aqueous raffinate III | 11.899 | 0.244 | 0.246 | 0.049 |
| Total metals extracted into organic phase (by difference) | 7.406 | 0.016 | 0.006 | 0.002 |
| Acid-Stripping of Metal-Loaded Ligand Solution |  |  |  |  |
| Acid strip liquors (150 g/liter $H_2SO_4$) | 2.413 | 0.009 | 0.003 | 0.002 |

EXAMPLE 39

A 50 ml portion of a 2.65% (weight/volume) solution of 6-n-butyl-4-(2'-tert.butyl-4'-methylphenoxy)quinoline-2-carboxylic acid in "Shellsol T" (equivalent to a cobalt concentration of 2 g/liter) was intimately contacted at room temperature for 10 minutes periods with 3 successive 50 ml portions of a solution of heavy metal sulphates in dilute sulphuric acid, initially at pH 2.0, in which the original concentrations of cobalt and iron (III) were 2.0 g/liter and those of zinc and copper were 0.2 and 0.05 g/liter respectively. After separation the metal ion concentrations in the three aqueous raffinates were then determined by atomic absorption spectrophotometry.

The metal-loaded organic layer subsequently was back-washed successively with 50 ml portions of dilute sulphuric acid in which the sulphuric acid concentrations were 30 g/liter and 150 g/liter respectively, and the metal concentrations in the two resultant acid extracts again were determined by the atomic absorption method. The results obtained were as follows.

|  | Metal Ion Concentration in Aqueous Liquor (g/liter) | | | |
| --- | --- | --- | --- | --- |
|  | Co | Fe(III) | Zn | Cu |
| Metal-Loading of Ligand Solution |  |  |  |  |
| Original solution of metal sulphates at pH 2.0 | 2.00 | 2.00 | 0.200 | 0.05 |
| Aqueous raffinate I | 1.94 | 1.44 | 0.197 | 0 |
| Aqueous raffinate II | 1.89 | 1.58 | 0.185 | 0.005 |
| Aqueous raffinate III | 1.96 | 2.07 | 0.196 | 0.008 |
| Total metals extracted into organic phase (by difference) | 0.21 | 0.91 | 0.022 | 0.138 |
| Acid-Stripping of Metal-Loaded Ligand Solution |  |  |  |  |
| Acid strip liquors (30 g/liter $H_2SO_4$) | 0.120 | 0.556 | 0.009 | 0.003 |
| Acid strip liquors (150 g/liter $H_2SO_4$) | 0.087 | 0.276 | 0.004 | 0.031 |
| Total metals extracted from loaded organic phase by 2 acid strips | 0.207 | 0.832 | 0.013 | 0.034 |

EXAMPLE 40

The procedure of Example 39 was repeated using 6-n-butyl-4-(2'-tert.butyl-5'-methylphenoxy)quinoline-2-carboxylic acid. The results are given in the following table.

|  | Metal Ion Concentration in Aqueous liquors (g/liter) | | | |
| --- | --- | --- | --- | --- |
|  | Co | Fe (III) | Zn | Cu |
| Metal-Loading of Ligand Solution |  |  |  |  |
| Original solution of metal sulphates at pH 2.0 | 2.00 | 2.00 | 0.200 | 0.05 |
| Aqueous raffinate I | 1.81 | 1.53 | 0.181 | 0.0003 |
| Aqueous raffinate II | 1.81 | 1.59 | 0.187 | 0.0024 |
| Aqueous raffinate III | 1.93 | 1.83 | 0.188 | 0.0012 |
| Total metals extracted into organic phase (by difference) | 0.45 | 1.05 | 0.044 | 0.1411 |
| Acid-Stripping of Metal-Loaded Ligand Solution |  |  |  |  |
| Acid strip liquors (30 g/liter $H_2SO_4$) | 0.089 | 0.702 | 0.008 | 0.0025 |
| Acid Strip liquors (150 g/liter $H_2SO_4$) | 0.228 | 0.263 | 0.018 | 0.029 |
| Total metals extracted from loaded organic phase by 2 acid strips | 0.317 | 0.965 | 0.026 | 0.0315 |

EXAMPLE 41

The procedure of Example 39 was repeated using a 3.13% (weight/volume) solution of 6-n-butyl-4-(2':4'-di-tert-pentylphenoxy) quinoline-2-carboxylic acid in "Shellsol T" (equivalent to a cobalt concentration of 2 g/liter). The results obtained were as follows.

|  | Metal Ion Concentrations in Aqueous Liquors (g/liter) | | | |
| --- | --- | --- | --- | --- |
|  | Co | Fe(III) | Zn | Cu |
| Metal-Loading of Ligand Solution | | | | |
| Original solution of metal sulphates at pH 2.0 | 2.00 | 2.00 | 0.200 | 0.05 |
| Aqueous raffinate I | 1.80 | 1.35 | 0.180 | 0.00 |
| Aqueous raffinate II | 1.98 | 1.69 | 0.190 | 2.1 ppm |
| Aqueous raffinate III | 1.95 | 1.94 | 0.190 | 3.04 ppm |
| Total metals extracted into organic phase (by difference) | 0.27 | 1.02 | 0.04 | 0.15 |
| Acid-Stripping of Metal-Loaded Ligand Solution | | | | |
| Acid strip liquors (30 g/liter $H_2SO_4$) | 0.17 | 0.89 | 0.01 | 0.0031 |
| Acid strip liquors (150 g/liter $H_2SO_4$) | 0.063 | 0.13 | 0.002 | 0.054 |
| Total metals extracted from loaded phase by 2 acid strips | 0.233 | 1.02 | 0.012 | 0.0571 |

EXAMPLE 42

The procedure of Example 39 was repeated using a 4.13% (weight/volume) solution of 4,6-(4'-nonylphenoxy)quinoline-2-carboxylic acid in "Shellsol T" (equivalent to a cobalt concentration of 2 g/liter). The following results were obtained.

|  | Metal Ion Concentration in Aqueous Liquors (g/liter) | | | | pH |
| --- | --- | --- | --- | --- | --- |
|  | Co | Fe(III) | Zn | Cu | |
| Metal-loading of Ligand Solution | | | | | |
| Original solution of metal sulphates at pH 2.0 | 2.00 | 2.00 | 0.20 | 0.05 | 2.0 |
| Aqueous raffinate I | 1.87 | 0.736 | 0.166 | 0.0005 | 1.45 |
| Aqueous raffinate II | 2.00 | 1.713 | 0.18 | 0.0045 | 1.79 |
| Aqueous raffinate III | 2.00 | 2.005 | 0.18 | 0.0057 | 2.0 |
| Total metals extracted into organic phase (by difference) | 0.13 | 1.546 | 0.074 | 0.1393 | |
| Acid-Stripping of Metal-loaded Ligand Solution | | | | | |
| Acid strip liquors (30 g/liter $H_2SO_4$) | 0.078 | 1.317 | 0.005 | 0.0036 | |
| Acid strip liquors (150 g/liter $H_2SO_4$) | 0.022 | 0.179 | 0.002 | 0.065 | |
| Total metals extracted from loaded phase by 2 acid strips | 0.10 | 1.496 | 0.007 | 0.0686 | |

EXAMPLE 43

A 50 ml portion of a 12.4% (weight/volume) solution of 4,6-di-(4'-nonylphenoxy)quinoline-2-carboxylic acid in "Shellsol T" (equivalent to a cobalt concentration of 5 g/liter) was intimately contacted at room temperature for 10 minute periods with three successive 150 ml portions of a solution of heavy metal sulphates in dilute sulphuric acid initially at pH 2.0, in which the original concentrations of cobalt and iron (II) ions were 2 g/liter and those of zinc and copper were 0.2 g/liter and 0.05 g/liter respectively. After separation the metal ion concentrations in the three aqueous raffinates were determined by atomic absorption spectrophotometry.

The metal-loaded organic solution was divided into 2 portions of equal volume, one of which was well-washed for 5 minutes with a 25 ml portion of sulphuric acid of strength 30 g/liter, whilst the second was treated similarly with sulphuric acid of strength 150 g/liter, the metal concentrations in both acid washings then being determined by the atomic absorption method. The results are given in the following table.

|  | Metal Ion Concentrations in Aqueous Liquors (g/liter) | | | |
|---|---|---|---|---|
|  | co | Fe(II) | Zn | Cu |
| Metal-Loading of Ligand Solution | | | | |
| Original solution of metal sulphates at pH 2.0 | 2.00 | 2.00 | 0.20 | 0.05 |
| Aqueous raffinate I | 1.52 | 1.67 | 0.136 | 0 |
| Aqueous raffinate II | 1.89 | 1.79 | 0.175 | 0 |
| Aqueous raffinate III | 2.03 | 1.84 | 0.189 | 0 |
| Total metals extracted into organic phase (by difference) | 1.68 | 2.10 | 0.300 | 0.45 |
| Acid-Stripping of Metal-loaded Ligand Solution | | | | |
| Acid strip liquors (30 g/liter $H_2SO_4$) | 1.46 | 1.27 | 0.117 | 0.037 |
| Acid strip liquors (150 g/liter $H_2SO_4$) | 1.51 | 1.90 | 0.120 | 0.076 |

EXAMPLE 44

The procedure of Example 38 was repeated using a 16.88% (weight/volume) solution of 6-methoxy-4-(4'-dodecylbenzyloxy)quinoline-2-carboxylic acid in chloroform (equivalent to a copper concentration of 11.25 g/liter). The results are given in the following table.

|  | METAL ION CONCENTRATION IN AQUEOUS LIQUORS (g/liter) | | | |
|---|---|---|---|---|
|  | Cu | Fe(III) | Co | Zn |
| Metal-Loading of Ligand Solution | | | | |
| Original solution of metal sulphates at pH 2.0 | 11.250 | 0.500 | 0.500 | 0.050 |
| Aqueous raffinate I | 1.578 | 0.500 | 0.500 | 0.050 |
| Aqueous raffinate II | 11.250 | 0.500 | 0.500 | 0.0489 |
| Aqueous raffinate III | 11.250 | 0.500 | 0.500 | 0.05 |
| Total metals extracted into organic phase (by difference) | 9.672 | 0 | 0 | 0.0011 |
| Acid-Stripping of Metal-Loaded Ligand Solution | | | | |
| Acid strip liquors (150 g/liter $H_2SO_4$) | 4.572 | 0 | 0 | 0.0008 |

EXAMPLE 45

A 25 ml portion of a 3.13% (weight/volume) solution of 8-methyl-4-(4'-dodecylbenzyloxy)quinoline-2-carboxylic acid in chloroform (equivalent to a cobalt concentration of 2 g/liter) was intimately contacted at room temperature for 10 minutes with 25 ml of a solution buffered at pH 5.0 by means of sodium acetate/acetic acid in which the original concentration of copper was 2 g/liter, that of cobalt was 0.2 g/liter, those of iron (II) and iron (III) were 0.1 g/liter, and that of zinc was 0.02 g/liter. After separation the metal ion concentration in the aqueous raffinate then was determined by atomic absorption spectrophotometry.

The metal-loaded organic layer subsequently was back-washed with 25 ml of dilute sulphuric acid of strength 150 g/liter, and the metal concentration in the acid extract determined by the atomic absorption method. Results are summarised as follows.

|  | Metal Ion Concentration in Aqueous Liquors (g/liter) | | | | |
|---|---|---|---|---|---|
|  | Cu | Fe(II) + Fe(III) | Co | Zn | pH |
| Metal-Loading of Ligand Solution | | | | | |
| Original solution of metal sulphates at pH 4.0 | 2.00 | 0.2 | 0.2 | 0.02 | 4.0 |
| Aqueous raffinate I | 0.317 | 0.203 | 0.1984 | 0.00857 | 4.0 |
| Aqueous raffinate II | 1.450 | 0.196 | 0.1935 | 0.01714 | 4.0 |
| Aqueous raffinate III | 1.860 | 0.197 | 0.2010 | 0.0143 | 4.0 |
| Total metals extracted into organic phase (by difference) | 2.373 | 0.004 | 0.0071 | 0.020 | |
| Acid-Stripping of Metal-loaded Ligand solution | | | | | |
| Acid strip liquors (150 g/liter $H_2SO_4$) | 1.810 | 0.0019 | 0.94 ppm | 0.020 | |

EXAMPLE 46

The procedure of Example 45 was repeated using a solution which contained no copper but in which iron (II), iron (III), cobalt and zinc were present at the same concentrations as previously. The results are given in the following table.

|  | Metal Ion Concentration in Aqueous Liquors (g/liter) | | | |
|---|---|---|---|---|
|  | Fe(II)+Fe(III) | Co | Zn | pH |
| Metal-Loading of Ligand Solution | | | | |
| Original solution of metal sulphates at pH 4.0 | 0.20 | 0.20 | 0.020 | 4.0 |
| Aqueous raffinate I | 0.187 | 0.1889 | 0.01646 | 4.0 |
| Aqueous raffinate II | 0.196 | 0.1889 | 0.01717 | 4.0 |
| Aqueous raffinate III | 0.192 | 0.1949 | 0.01734 | 4.0 |
| Total metals extracted into organic phase (by difference) | 0.025 | 0.0273 | 0.00903 | |
| Acid-stripping of metal-loaded Ligand solution | | | | |
| Acid strip liquors (150 g/liter H$_2$SO$_4$) | 0.0041 | 0.0019 | 0.00181 | |

EXAMPLE 47

A 25 ml portion of a 3.82% (weight/volume) solution of 8-methyl-4-(4'-nonylphenoxy)quinoline-2-carboxylic acid in chloroform (equivalent to a copper concentration of 3 g/liter) was intimately contacted at room temperature for 10 minutes with 25 ml of a solution buffered at 4.0 by means of sodium acetate/acetic acid in which the original concentration of copper was 2 g/liter, that of cobalt was 0.2 g/liter, those of iron (II) and iron (III) were 0.1 g/liter, and that of zinc was 0.02 g/liter. After separation the metal ion concentration in the aqueous raffinate was then determined by atomic absorption spectrophotometry.

The metal-loaded organic layer was subsequently back-washed with 25 ml of dilute sulphuric acid of strength 150 g/liter, and the metal concentration in the acid extract was determined by the atomic absorption method. The results obtained were as follows.

|  | Metal Ion Concentration in Aqueous Liquors (g/liter) | | | |
|---|---|---|---|---|
|  | Cu | Fe(II)+Fe(III) | Co | Zn |
| Original solution of metal sulphates at pH 2.0 | 2.00 | 0.20 | 0.20 | 0.02 |
| Aqueous raffinate | 0.57 | 0.20 | 0.20 | 0.02 |
| Total metals extracted into organic phase (by difference) | 1.43 | 0 | 0 | 0 |
| Total metals extracted from loaded organic phase by 150 g/liter H$_2$SO$_4$ | 1.33 | 1 ppm | 0.62 ppm | 0.2 ppm |

EXAMPLE 48

A 25 ml portion of a solution of copper sulphate and dilute sulphuric acid initially at pH 2.0 and with a copper concentration of 12 g/liter, was intimately contacted at room temperature for 5 minute periods with 3 successive 25 ml portions of a 16.11% (weight/volume) solution of 3-n-propyl-6-n-butyl-4-isodecyloxyquinoline-2-carboxylic acid in "Escaid 110" (a mainly aliphatic kerosine) (equivalent to a copper concentration of 12 g/liter). After separation the metal concentration and pH of the aqueous phase was determined after each contacting and the results were as follows:

| Aqueous Solution | Cu Content (g/liter) | pH |
|---|---|---|
| Initially | 12.0 | 2.0 |
| After 1st ligand treatment | 2.21 | 0.95 |
| After 2nd ligand treatment | 0.07 | 0.73 |
| After 3rd ligand treatment | 0.006 | 0.60 |

EXAMPLE 49

A 25 ml portion of a 5.37% (weight/volume) solution of 3-n-propyl-6-n-butyl-4-isodecyloxyquinoline-2-carboxylic acid in "Escaid 110" (equivalent to a copper concentration of 4 g/liter) was intimately contacted for 10 minute periods with 3 successive 25 ml portions of a solution of heavy metal sulphates in dilute sulphuric acid initially at pH 2.0 in which the original concentrations of copper, iron (III), cobalt and zinc were 8.0, 4.0, 2.0 and 0.2 g/liter respectively. After separation the metal ion ooncentrations in the three aqueous raffinates then were determined by atomic absorption spectrophotometry.

The metal loaded organic layer subsequently was back-washed with a 25 ml portion of 25% (weight/volume) hydrochloric acid, and the metal ion concentration in the acidic strip liquors was determined by the atomic absorption method. The results are given in the following table.

| | Metal Ion Concentration in Aqueous liquors (g/liter) | | | |
|---|---|---|---|---|
| | Cu | Fe(III) | Co | Zn |
| Metal-Loading of Ligand Solution | | | | |
| Original solution of metal sulphates at pH 2.0 | 8.0 | 4.0 | 2.0 | 0.2 |
| Aqueous raffinate I | 4.507 | 4.0 | 2.0 | 0.2 |
| Aqueous raffinate II | 7.302 | 4.0 | 2.0 | 0.2 |
| Aqueous raffinate III | 7.760 | 4.0 | 2.0 | 0.2 |
| Total metals extracted into organic phase (by difference) | 4.431 | 0 | 0 | 0 |
| Acid-Stripping of Metal-loaded Ligand solution | | | | |
| Acid strip liquors (25% w/v HCl) | 3.710 | 9.5 ppm | 4.5 ppm | 0.65 ppm |

EXAMPLE 50

The procedure of Example 49 was repeated with a solution which contained no copper but otherwise was similar to that used previously. Results were as follows.

| | Metal Ion Concentration in Aqueous Liquors (g/liter) | | |
|---|---|---|---|
| | Fe(III) | Co | Zn |
| Metal-Loading of Ligand Solution | | | |
| Original solution of metal sulphates at pH 2.0 | 4.0 | 2.0 | 0.2 |
| Aqueous raffinate I | 3.0 | 2.0 | 0.2 |
| Aqueous raffinate II | 2.45 | 2.0 | 0.2 |
| Aqueous raffinate III | 3.076 | 2.0 | 0.2 |
| Total metals extracted into organic phase (by difference) | 3.474 | 0 | 0 |
| Acid-Stripping of Metal-Loaded Ligand Solution | | | |
| Acid strip liquors (25% w/v HCl) | 3.143 | 12 ppm | 1.3 ppm |

We claim:
1. A quinoline-2-carboxylic acid of the formula

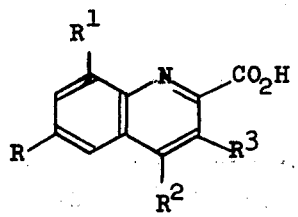

wherein R is a methoxy group or an alkyl group containing up to 12 carbon atoms, $R^1$ is a hydrogen atom or a methyl group, $R^2$ is a branched chain alkoxy group containing up to 12 carbon atoms, a phenoxy group substituted by one or two alkyl groups containing a total of not more than 12 carbon atoms or a benzyloxy group substituted by one or two alkyl groups containing a total of not more than 12 carbon atoms, and $R^3$ is a hydrogen atom or a n-propyl group.

2. A quinoline-2-carboxylic acid as claimed in claim 1 wherein the groups, R, $R^1$, $R^2$ and $R^3$ contain a total of from 6 to 20 aliphatic carbon atoms.

3. A quinoline-2-carboxylic acid as claimed in claim 1 wherein the group $R^2$ is an isodecyloxy group.

4. A quinoline-2-carboxylic acid as claimed in claim 1 which is 3-n-propyl-6-n-butyl-4-isodecyloxyquinoline-2-carboxylic acid.

* * * * *